United States Patent [19] [11] 4,193,922
Agócs et al. [45] Mar. 18, 1980

[54] SUBSTITUTED-1,2,4-OXADIAZOLIDINE-3-ONE DERIVATIVES

[75] Inventors: Pál Agócs, Szeged; István Fábián, Sajószentpéter; András Gajdacsi, Szeged; Sandor Nagy; Zoltán Pintér, both of Miskolc, all of Hungary

[73] Assignee: Északmagyarországi Vegyimüvek, Sajóbábony, Hungary

[21] Appl. No.: 693,892

[22] Filed: Jun. 8, 1976

[30] Foreign Application Priority Data

Jun. 9, 1975 [HU] Hungary ............................... EA 148

[51] Int. Cl.² .......................................... C07D 271/06
[52] U.S. Cl. ..................................... 548/132; 424/272
[58] Field of Search ................... 260/307 A; 424/272; 71/92

[56] References Cited

U.S. PATENT DOCUMENTS 2,852,523   9/1958   Lopresti et al. ...................... 260/307

Primary Examiner—Jose Tovar
Attorney, Agent, or Firm—Karl F. Ross

[57] ABSTRACT

Herbicidal and fungicidal compounds of the formula

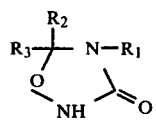

wherein $R_1$ is substituted or unsubstituted phenyl or naphthyl and $R_2$ and $R_3$ are the same or different and are $C_1$-$C_5$ alkyl or from a five- or six-membered ring.

8 Claims, 1 Drawing Figure

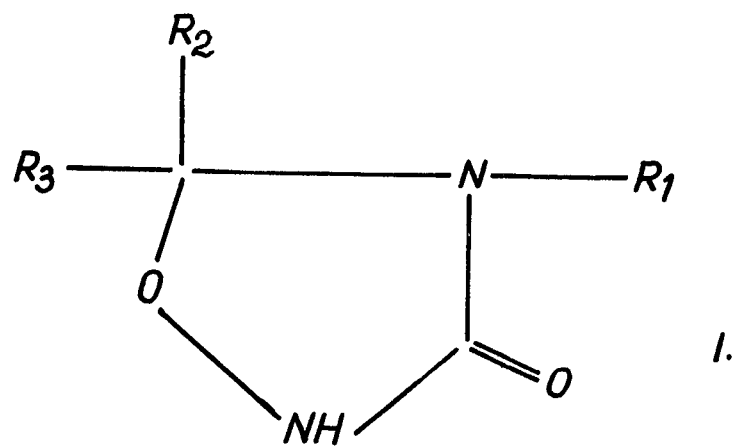
I.
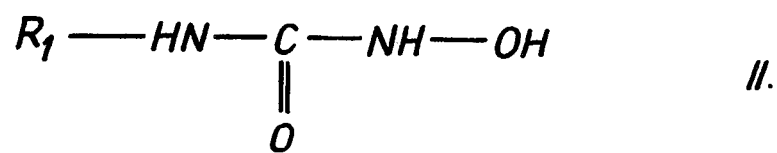
II.
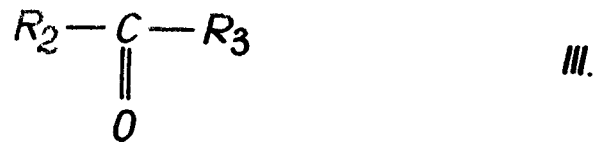
III.

SUBSTITUTED-1,2,4-OXADIAZOLIDINE-3-ONE DERIVATIVES

This invention relates to compounds useful as pesticides. The new compounds of the invention are derivatives of 1,2,4-oxadiazolidine-3-one and have the formula I

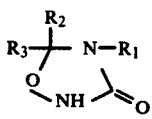

wherein $R_1$ is a phenyl or naphthyl group, unsubstituted or substituted with one or two halogens, $C_{1-4}$ alkyl, alkoxy or nitro groups, $R_2$ and $R_3$ are the same or different and represent an alkyl group containing 1 to 5 carbon atoms, or form a $(CH_2)_n$ group together—where n is 4 or 5, forming thus a 5 or 6 membered ring.

The present invention also provides a process for the preparation of the biologically active compounds of the formula I. Five-membered heterocyclic compounds containing 2 nitrogens and 1 oxygen in the ring, possessing biological activity such as weed killer activity are known from British Patent Specifications Nos.: 1,051,322, 1,057,955, 1,063,789, 1,094,:977, 1,099,101, 1,110,500, 1,142,917, 1,168,721, 1,173,300, 1,198,726, 1,208,111, 1,208,112, 1,211,556, 1,286,067.

The compounds of the general formula I are preferably prepared by reacting a hydroxy-urea compound of the formula III

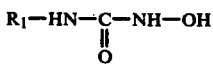

where $R_1$ is as defined above—with a ketone of the formula II

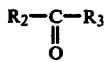

wherein $R_2$ and $R_3$ are identical or different and are as defined above.

The reaction is preferably carried out in an inert solvent or using the ketone as a solvent at a temperature ranging from room temperature to the boiling point of the solvent or of the ketone, if desired, a water binding agent can be used.

Some of the new compounds of the formula I are phytotoxic and can be thus useful as herbicides. Some compounds of the invention display fungicide activity and some are useful against insects. The new 1,2,4-oxadiazolidine-3-one derivatives are solid crystalline substances, which can be further worked up to pesticidal compositions in the form of wettable powders, emulsion concentrates, aqueous or oily suspensions etc.

The invention is further illustrated with the following non-limiting Examples.

EXAMPLE 1

4-(3,4-Dichlorophenyl)-5,5-dimethyl-1,2,4-oxazolidine-3-one 22.1 g (0.1 mole) of N-(3,4-dichlorophenyl)-N'-hydroxy-urea and 130 g. of acetone are added to a flask of a volume of 500 ml. The mixture is heated under stirring and stirred for 15 minutes under reflux.

The reaction mixture is then cooled to 0° C. and the precipitated crystalline substance is filtered and recrystallized from the mixture of acetone and pethroleum ether.

23.5 g. of crystalline substance are obtained, m.p. 73°–75° C.

Yield: 90%

Analysis

Calculated: %C, 46.0; %H, 3.68; %N, 10.73; %Cl, 27.12. Found: %C, 45.84; %H, 4.03; %N, 10.42; %Cl, 26.98.

EXAMPLE 2

4-(3-Chlorophenyl)-5,5-spiro-pentamethylene-1,2,4-oxadiazolidine-3-one 18.6 g. (0.1 moles) of N-(3-chlorophenyl)-N'-hydroxy-urea are dissolved in the mixture of 60 g. of cyclohexanone and 100 ml. of benzene. The solution is stirred for 5 hours on a water bath at reflux temperature. The reaction mixture is evaporated and the residue is recrystallized from the mixture of methanol and water.

22.6 g. of crystalline product are obtained, m.p. 125° C.

Yield: 85%.

Analysis

Calculated: %C, 58.54; %H, 5.67; %N, 10.51; %Cl, 13.29. Found: %C, 58.35; %H, 5.67; %N, 10.54; %Cl, 13.10.

EXAMPLE 3

4-(3-Chlorophenyl)-5,5-dimethyl-1,2,4-oxadiazolidine-3-one 18.6 g. (0.1 moles) of N-(3-chlorophenyl)-N'-hydroxy-urea are added to 130 g. of acetone. The mixture is stirred for 15 minutes at the temperature of the water bath under reflux. The reaction mixture is then evaporated to dryness and the residue is recrystallized from the mixture of acetone and water.

20.8 g. of crystalline substance are obtained, m.p. 84°–85° C.

Yield: 92%.

Analysis

Calculated: %C, 52.99; %H, 4.89; %N, 12.36; %Cl, 15.64. Found: %C, 52.63; %H, 4.60; %N, 12.28; %Cl, 15.53.

EXAMPLE 4

4-(3-Chlorophenyl)-5,5-dimethyl-1,2,4-oxadiazolidine-3-one

The product is prepared according to the procedure set forth in Example 3, but the reaction mixture is stirred at room temperature for 24 hours. After recrystallization 20.3 g. of the product are obtained, m.p. 84°–85° C.

Yield: 81%.

Analysis is identical with that of Example 3.

EXAMPLE 5

4-(3-Chlorophenyl)-5,5-diethyl-1,2,4-oxadiazolidine-3-one 18.7 g. of N-(3-chlorophenyl)-N'-hydroxy-urea are added to 116 g. of diethyl ketone. The reaction is stirred at 90° C. for 1 hour. The reaction mixture is then evaporated to dryness and the residue is recrystallized from a mixture of methanol and water.

22.7 g. of crystalline substance are obtained, m.p. 82° C.

Yield: 89%.

Analysis

Calculated: %C, 56.59; %H, 5.94; %N, 11.00; %Cl, 13.92. Found: %C, 56.61; %H, 6.07; %N, 11.27; %Cl, 13.60.

Similarly the following compounds of the present invention were prepared:

| No. | Compound | m.p. | Yield: |
|---|---|---|---|
| 6. | 4-Phenyl-5,5-dimethyl-1,2,4-oxadiazolidine-3-one | 109 | 81.5 |
| 7. | 4-(2-Chlorphenyl)-5,5-dimethyl-1,2,4-oxadiazolidine-3-one | 82 | 78.0 |
| 8. | 4-(4-Chlorphenyl)-5,5-dimethyl-1,2,4-oxadiazolidine-3-one | 116 | 86.0 |
| 9. | 4-(4-Bromphenyl)-5,5-dimethyl-1,2,4-oxadiazolidine-3-one | 135 | 91.5 |
| 10. | 4-(2-Methylphenyl)-5,5-dimethyl-1,2,4-oxadiazolidine-3-one | 75 | 79.5 |
| 11. | 4-(4-Methylphenyl)-5,5-dimethyl-1,2,4-oxadiazolidine-3-one | 112 | 87.5 |

The compounds of the invention are all crystalline substances, easy to grind and mix and to work up to pesticide compositions. Thus, for example, 50 kg. of a compound of the formula I can be admixed with 40 kg. of Ultrasil (trademark for amorphous silicon oxide) i.e. with a solid carrier, with 4 kg. of Totanin B (trademark for sulfite waste liquor powder) and with 2 kg. of Tenciofix LX Special (trademark for purified sulfite waste liquor powder) i.e. a dispersing agent, and with 4 kg. of Tensopol SP-USP (trademark for lauryl alcohol sulfate) i.e. a wetting powder, and the mixture is ground and the product is obtained in the form of a wettable powder.

EXAMPLE 12

The fungicidal activity of the new 1,2,4-oxazolidine-3-one derivatives was tested. 4-(3-chlorophenyl)-5,5-dimethyl-1,2,4-oxazolidine-3-one (Example 3), 4-(4-chlorophenyl)-5,5-dimethyl-1,2,4-oxazolidine-3-one (Example 8) and 4-(4-methylphenyl)-5,5-dimethyl-1,2,4-oxadiazolidine-3-one are dissolved in dimethylsulfoxide and a 1% solution is prepared. By diluting the solution the minimal inhibiting concentration was determined.

The tested fungi were as follows:

*Alternaria tenuis*
*Fusarium culmorum*
*Botrytis allii*

The test was conducted in Petri plates using agar diffusion method and as minimal concentration that dilution concentration was considered, at which the inhibited zone did not change during 72 hours.

According to our observations the product Example 3 inhibited the growth of *Alternaria tenuis* even at a concentration of 40 ppm., the compound of Example 8 inhibited the growth of *Botrytis allii* at 100 ppm., the growth of *Fusarium culmorum* at 20 ppm., the compound of Example 11 inhibited the growth of *Fusarium culmorum* at 50 ppm., and the growth of *Alternaria tenuis* at 100 ppm.

EXAMPLE 13

The herbicidal activity of the 1,2,4-oxadiazolidine-3-one derivatives on monocotyledons and dicotyledons was tested during a preemergent and postemergent treatment.

A 50% wettable powder was prepared from the new derivatives, and the treatment was carried out in the form of an aqueous suspension by applying a quantity corresponding to 3 kg./ha. each time.

The following weeds were tested:

Monocotyledons:
*Echinocloa crus-galli*
*Setaria viridis*

Dicotyledons:
*Amaranthus retroflexus*
*Chenopodium album*

The preemergent treatment was carried out before sprouting and the postemergent treatment was carried out in a 3–4 leaves state. The effectivity was evaluated 28 days after treatment and the numbers 1–5 have the following meaning:

1: 0–20% activity
2: 21–40% activity
3: 41–60% activity
4: 61–80% activity
5: 81–activity The results of the experiments were summarized in the following table:

| Compound of Example | Activity | | | |
|---|---|---|---|---|
| | Monocotyledons | | Dicotyledons | |
| | pre-emergent | post-emergent | pre-emergent | post-emergent |
| 1 | 4 | 2 | 3 | 1 |
| 2 | 5 | 2 | 4 | 2 |
| 6 | 3 | 1 | 5 | 1 |
| 9 | 4 | 2 | 3 | 1 |
| 10 | 4 | 2 | 4 | 1 |

We claim:
1. 4-(3,4-dichlorophenyl)-5,5-dimethyl-1,2,4-oxadiazolidine-3-one.
2. 4-(3-chlorophenyl)-5,5-spiro-pentamethylene-1,2,4-oxadiazolidine-3-one.
3. 4-(3-chlorophenyl)-5,5-dimethyl-1,2,4-oxadiazolidine-3-one.
4. 4-phenyl-5,5-dimethyl-1,2,4-oxadiazolidine-3-one.
5. 4-(4-chlorophenyl)-5,5-dimethyl-1,2,4-oxadiazolidine-3-one.
6. 4-(4-bromophenyl)-5,5-dimethyl-1,2,4-oxadiazolidine-3-one.
7. 4-(2-methylphenyl)-5,5-dimethyl-1,2,4-oxadiazolidine-3-one.
8. 4-(4-methylphenyl)-5,5-dimethyl-1,2,4-oxadiazolidine-3-one.